(12) United States Patent
Frova et al.

(10) Patent No.: US 6,767,355 B2
(45) Date of Patent: Jul. 27, 2004

(54) TRACHEOSTOMY DILATOR

(75) Inventors: Giulio Frova, Mailand (IT); Michael Quintel, Mannheim (DE); Werner Mailänder, Korb (DE); Heiko Kaczorowski, Stuttgart (DE); Gisbert Ranzinger, Aichwald (DE)

(73) Assignee: Willy Rusch GmbH, Kernen Rommelshausen (DE)

( * ) Notice: Subject to any disclaimer, the term of this patent is extended or adjusted under 35 U.S.C. 154(b) by 63 days.

(21) Appl. No.: 10/004,233

(22) Filed: Oct. 31, 2001

(65) Prior Publication Data

US 2002/0077655 A1 Jun. 20, 2002

(30) Foreign Application Priority Data

Nov. 3, 2000 (DE) .......................................... 100 54 527
Sep. 11, 2001 (DE) .......................................... 101 44 534

(51) Int. Cl.$^7$ ............................................ A61M 29/00
(52) U.S. Cl. ...................................... 606/191; 604/264
(58) Field of Search ................................ 606/184, 185, 606/191, 198; 604/164.01, 164.06, 164.1, 164.11, 264

(56) References Cited

U.S. PATENT DOCUMENTS 4,026,296 A     5/1977   Stoy
5,989,228 A  *  11/1999  Danks et al. ................ 604/264
6,436,119 B1 *  8/2002   Erb et al. ..................... 606/198
6,517,519 B1 *  2/2003   Rosen et al. ........... 604/164.06

FOREIGN PATENT DOCUMENTS

| DE | 1541237 | 7/1969 |
| DE | 0065604 | 7/2001 |
| EP | 0530595 | 3/1993 |
| GB | 2313316 | 11/1997 |
| WO | 9107202 | 5/1991 |
| WO | 9944665 | 9/1999 |

OTHER PUBLICATIONS

P. Ciaglia, M.D. F.C.C.P., Rita Firsching, R.N. and Cynthia Syniec, R.R.T. "Elective Percutaneous Dilational Tracheostomy" Chest —Jun., 1985—pp. 715–719.
B. Wolfgarten and M. July—"Punktionstracheotomie mit einmaliger Trachealdilatation"—Der Chirurg–2000—vol. 71, pp 63–65.

* cited by examiner

Primary Examiner—Kevin T. Truong
(74) Attorney, Agent, or Firm—Polster, Lieder, Woodruff & Lucchesi, L.C.

(57) ABSTRACT

A tracheostomy dilator comprises a rod which is penetrated by an inner lumen. Both ends of the inner lumen are open, at the end facing the patient and at the end of the tracheostomy dilator facing away from the patient. The end facing the patient is provided with a thread. The tracheostomy dilator is used as screw dilator and can widen the tissue in one single dilation process such that a further tracheostomy cannula can be inserted into the trachea.

11 Claims, 2 Drawing Sheets

TRACHEOSTOMY DILATOR

BACKGROUND OF THE INVENTION

The invention concerns a tracheostomy dilator consisting of a rod having an inner lumen which is open at both ends and extends from the end of the rod facing the patient to the end of the rod facing away from the patient.

Tracheostomy dilators of this type have become known in connection with puncture tracheostomy according to Ciaglia et al., "Elective Percutaneous Dilatational Tracheostomy" Chest 1985, volume 6, pages 715–719.

In the known puncture tracheostomy, the trachea is transcutanely punctured in a bronchoscopically controlled fashion, below the ring-like cartilage, preferably between the second and third tracheal ring, and successively extended via a Seldinger wire with stepped dilators, and after the desired extension, a tracheostomy cannula is inserted into the trachea. This tracheostomy method has been used in the meantime at least for a highly selective part of patients. The known method, however, also bears risks for the patient and consequently only very experienced anaesthetists are supposed to use this method. The known method is time-consuming and every dilation bears the danger of injuring the posterior tracheal wall.

A known further development of the percutaneous dilatation tracheostomy which has become known from Wolfgarten et al. "Punktionstracheostomie mit einmaliger Trachealdilatation" (puncture tracheostomy with single tracheal dilatation), Chirurg 2000, pages 63–65 and 723–724, consists e.g. in that the skin is cut between ring-like cartilage and incisura jugularis approximately at the height of the third tracheal ring. Subsequently, the skin tissue and cervical muscles are extended with a clamp until the trachea becomes visible. The trachea is punctured via the skin cut by means of a hollow needle under bronchoscopic control, a guiding wire is pushed under visual control into the trachea, and dilation by means of a conical dilator is effected once via the guiding wire to a size required for the tracheostomy cannula to be inserted.

It is a common feature of the known dilatation methods that the stoma channel and the anterior tracheal wall must be widened through a large feed force and long advancing distance. The tip of the dilator might come too close to the posterior tracheal wall and cause injuries.

For this reason, single bouginage seems to be less controllable than bouginage in several steps according to Ciaglia et al. since the feed forces for single bouginage are larger and the advancing distance can be better controlled via bouginage in several steps.

It is the object of the present invention to further develop the known tracheostomy dilators such that they can be used with improved control.

SUMMARY OF THE INVENTION

This object is achieved in accordance with the invention in that the end of the rod facing the patient comprises a first thread and the section of the rod comprising the first thread tapers towards the end facing the patient.

The inventive tracheostomy dilator therefore has the substantial advantage that during dilatation, also during single dilatation, the compression onto the anterior tracheal wall is reduced to a minimum. The inventive dilator is threaded onto a guiding wire which is inserted, in a fashion known per se, into the trachea, and then screwed into the tissue until it has penetrated the trachea in the desired manner. The user must not exert a feed impulse in the transverse direction onto the inventive dilator since the thread automatically produces a feeding motion of the dilator in correspondence with the selected thread pitch.

The inventive dilator penetrates the anterior tracheal wall in a smooth fashion compared to conventional dilatation which includes substantially large feed forces and protrudes the anterior wall of the inner lumen of the trachea such that the dilator tip possibly reaches a dangerous closeness to the posterior tracheal wall. The inventive dilator does not pose this danger since dilatation is carried out in a helical motion. Only dilatation is desired and not any compression of the tracheal wall which would be dangerous. Dilatation with screws minimizes compression onto the anterior tracheal wall. The feed forces for screw dilatation can be controlled to a large extent through turning of the dilator and are predetermined by the selected thread pitch. This ensures continuous dilatation in the radial direction without exerting too high an axial pressure onto the tissue to be dilated.

The rod in accordance with the invention tapers in the rod section comprising the thread towards the free end of the rod facing the patient. This is advantageous in that the tissue to be widened is smoothly stretched. Depending on the conical tapering of this section, dilatation is effected on a shorter or longer stretch.

Moreover, in a preferred embodiment of the inventive tracheostomy dilator, the first thread is formed as automatically cutting thread. This is advantageous in that the dilator can penetrate, e.g. be turned, into the tissue to be widened with little external force.

If the first thread of the tracheostomy dilator has different thread pitches across its length, it is possible to produce only slight expansion of the tissue in a first dilatation step by turning the dilator several times, and to produce larger dilatation with a smaller turning motion, accompanied by a larger axial advance, e.g. in a second dilatation step, wherein the thread tip of the inventive dilator is fixedly anchored in the tissue.

If the free end of the rod facing the patient is additionally chamfered, the dilator tip penetrates the tissue bordering the tip in a particularly smooth fashion.

In a preferred fashion, the diameter of the inner lumen is adjusted to the outer diameter of a guiding wire such that the inner volume is filled by the guiding wire without leaving any gaps. This is advantageous in that tissue cannot reach the inner lumen during dilatation.

The rod can also comprise a second thread connecting to the first thread which permits further controlled advance of the dilator. Additionally, the dilator is fixed in its position by the second thread. The second thread can extend to the end facing away from the patient, i.e. along the entire cylindrical shaft or only in the section of the cylindrical shaft facing the patient. The thread pitch can correspond to the pitch of the first thread or be different. It is also feasible that the thread pitch of the second thread varies along the shaft. The second pitch can be formed as a bar disposed onto the shaft or as depression in the bar wall.

In a further embodiment of the inventive tracheostomy dilator, the first and/or second thread has a surface showing little friction when contacting tissue. This has the advantage that, when turning the inventive dilator, tissue cannot be threaded onto the thread pitches. It is particularly advantageous to provide a hydrophilic layer on the outer surface and/or wet the outer surface with a sliding gel. Through provision of such friction-reducing measures, the thread section of the dilator can be turned into the tissue to be dilated with little force and in a controlled manner.

To trigger a controlled turning motion of the dilator, the end of the rod facing away from the patient is preferably provided with a handle to permit controlled turning of the inventive screw dilator by the user.

If the inventive tracheostomy dilator is produced from boil proof plastic or metal it can be sterilized a few times rather than disposed of after use.

In another embodiment of the invention, the tracheostomy dilator can be produced from two semi-shells which are connected to one another for the dilatation process either via a film hinge or in another fashion. When dilatation is finished, the screw dilator can be withdrawn after positioning of the tracheostomy cannula and be removed from the guiding wire outside of the patient. This embodiment has the advantage that the screw dilator must not be withdrawn across the entire length of the guiding wire.

In a further inventive embodiment, a tracheostomy cannula can be disposed on the outer surface of the inventive screw dilator. This has the advantage that the tracheostomy cannula is advanced into the trachea during dilatation.

The inventive screw dilator reduces the still present risks of a percutaneous dilatation tracheostomy since dilatation is triggered through a radial motion component.

Further advantages can be extracted from the description and the enclosed drawing. The features mentioned above and below can be used in accordance with the invention either individually or collectively in any arbitrary combination. The embodiment described below is to be understood as exemplary representation of an inventive tracheostomy dilator. The embodiment shown in the figures is highly schematised and not to be taken to scale.

DESCRIPTION OF THE PREFERRED EMBODIMENT

Figure 1:
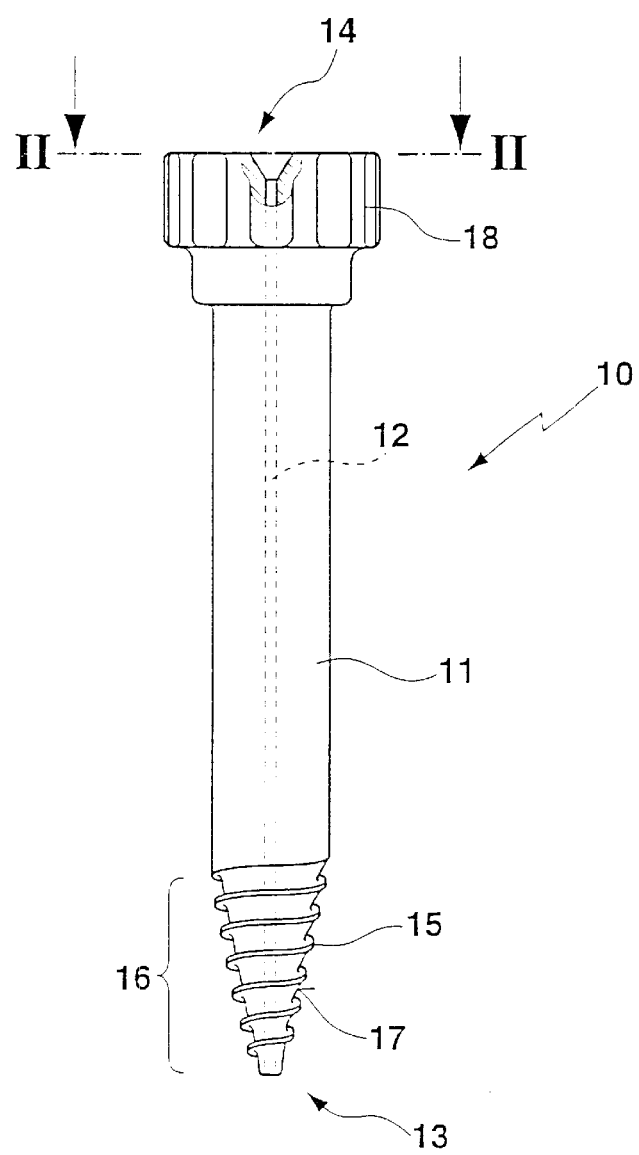
FIG. 1 is a side view of an inventive tracheostomy dilator.

In FIG. 1, 10 designates a tracheostomy dilator which is formed of a rod 11 with inner lumen 12. The rod 11 is produced from a bending-resistant material such as boil proof plastic material or metal. In further embodiments, the rod 11 may also be bent. The inner lumen 12 runs through the rod 11 in an axial direction and is formed as passage/transitional lumen which permits introduction of a guiding wire (not shown in FIG. 1) through the rod 11.

The tracheostomy dilator 10 tapers at the end 13 facing the patient and a guiding wire can be inserted into the free end which projects from the tracheostomy dilator 10 at the end facing away from the patient. Additionally, the end 13 facing the patient is provided with a first thread 15 which extends across a section 16. The first thread 15 can have different thread pitches across the axial extension of the first thread 15 and be formed such that it cuts automatically. The free tip is chamfered at the end 13 facing the patient.

An outer surface 17 of the first thread 15 is preferably smooth to prevent tissue from sticking to the thread pitches. The outer surface 17 can additionally have a hydrophilic layer and/or be wetted with gel.

The end 14 facing away from the patient is provided with a handle 18 to facilitate gripping and controlled turning of the tracheostomy dilator 10 when required.

Figure 2:
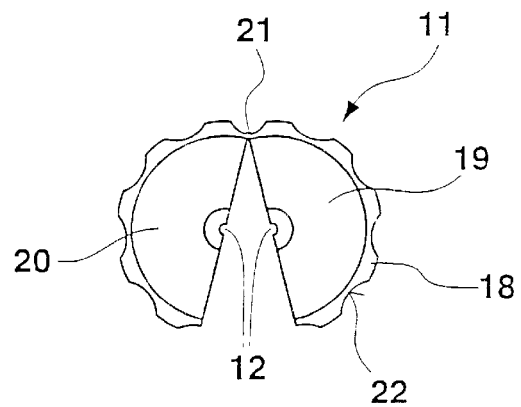
FIG. 2 is a top view of a further dividable embodiment according to line II—II of FIG. 1.

FIG. 2 shows the tracheostomy dilator 10 from FIG. 1 in another dividable embodiment, seen from the top according to the line II—II of FIG. 1. The rod 11 is composed of a first semi-shell 19 and a second semi-shell 20 which are held together by a film hinge 21. When the semi-shells 19,20 are unfolded, the inner lumen 12 is divided and a guiding wire disposed in the inner lumen 12 can be removed from the tracheostomy dilator. The handle 18 has contours or grooves 22 that the user can hold to facilitate turning of the tracheostomy dilator in a controlled fashion.

Figure 3:
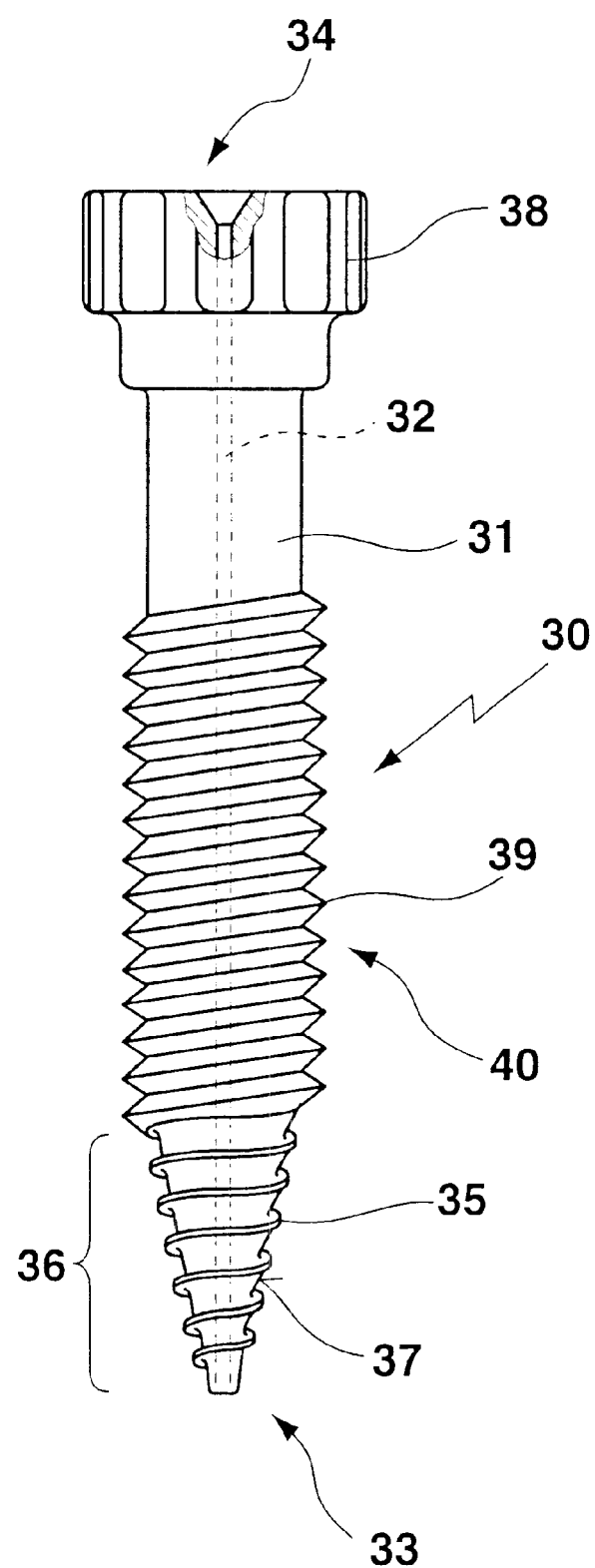
FIG. 3 is a side view of a second embodiment of an inventive tracheostomy dilator.

FIG. 3 shows a tracheostomy dilator 30 which is formed of a rod 31 having an inner lumen 32. The rod 31 consists of a bending-resistant material, e.g. a boil proof plastic material or metal. In other embodiments, the rod 31 can be bent. The inner lumen 32 runs through the rod 31 in the axial direction and is formed as a passing lumen such that a guiding wire (not shown in FIG. 3) can be pushed through the rod 31.

The end 33 of the tracheostomy dilator 30 facing the patient is tapered and a guiding wire can be inserted into the free end which projects from the tracheostomy dilator 30 at the end 34 facing away from the patient. The end 33 facing the patient additionally comprises a first thread 35 which extends over a section 36. The first thread 35 may have different thread pitches over the axial extension of the first thread 35 and be formed such that it has automatic cutting properties. The free tip is chamfered at the end 33 facing the patient.

An outer surface 37 of the first thread 35 is preferably smooth to prevent tissue from sticking to the thread pitches. The outer surface 37 can have additionally a hydrophilic layer and/or be wetted with a gel.

The end 34 facing away from the patient is provided with a handle 38 to facilitate gripping and controlled turning of the tracheostomy dilator 30 when required.

A second thread 39 connects to the first thread 35 which is formed on the cylindrical shaft section 40 of the rod 31. In this example, the second thread 39 extends over only part of the cylindrical shaft section 40.

A tracheostomy dilator 10 comprises a rod 11 which is penetrated by an inner lumen 12. The inner lumen 12 is open both at the end 13 facing the patient and at the end 14 of the tracheostomy dilator 10 facing away from the patient. The end 13 facing the patient is provided with a thread 15. The tracheostomy dilator 10 is used as screw dilator and can widen the tissue in one dilatation process such that a tracheostomy cannula can be inserted in the trachea.

We claim:

1. A tracheostomy dilator comprising a rod having a first cutting end facing the patient and a second gripping end facing away from the patient, an inner lumen which is open at both ends of the rod and extends from the first end to the second end of the rod, a threaded section at said first end, the threaded section of the rod tapering towards a free end of the rod and being a cutting thread; said threaded section being coated with a hydrophilic layer and/or a sliding gel.

2. The tracheostomy dilator according to claim 1, wherein the thread has different pitches across its length.

3. The tracheostomy dilator according to claim 1, wherein the free end of the rod facing the patient is chamfered.

4. The tracheostomy dilator according to claim 1, wherein the diameter of the inner lumen corresponds substantially to the outer diameter of a guiding wire.

5. The tracheostomy dilator according to claim 1 wherein said thread on said tapered portion comprises a first thread, said tracheostomy dilator further including a second thread on said rod above said first thread.

6. The tracheostomy dilator according to claim 5 wherein said second thread has an outer surface which shows little friction when contacting tissue.

7. The tracheostomy dilator according to claim 1, wherein a tracheostomy cannula is disposed on the outer surface of the rod.

8. A tracheostomy dilator comprising a rod having a first end facing the patient and a second end facing away from the patient, an inner lumen which is open at both ends of the rod and extends from the first end to the second end of the rod, a threaded section at said first end, the threaded section of the rod tapering towards a free end of the rod; wherein the rod comprises two shell segments which are capable of being separated from each other.

9. A tracheostomy dilator comprising a rod having a first end which faces a patient and a second gripping end which faces away from the patient, an inner lumen which is open at the ends of said rod and extends from the first end to the second gripping end of the rod, a first thread at the first end of the rod, the section of the rod which is provided with the first thread tapering towards a free end of the rod, and a second thread on said rod positioned below said second, gripping end and adjacent said first thread; said first thread being a cutting thread adapted to cut into a patient and said second thread being a positioning thread adapted to maintain the position of said dilator relative to a patient upon insertion of the dilator into a patient; at least one of said first and second threads being coated with a hydrophilic layer and/or a sliding gel.

10. The tracheostomy dilator of claim 9 wherein said rod is produced from a boil proof plastic material or metal.

11. The tracheostomy dilator of claim 9 wherein said second thread connects to said first thread.

\* \* \* \* \*